US005409817A

United States Patent [19]
Ito et al.

[11] Patent Number: 5,409,817
[45] Date of Patent: Apr. 25, 1995

[54] USE OF TRANS-SIALIDASE AND SIALYLTRANSFERASE FOR SYNTHESIS OF SIALYLα2→3βGALACTOSIDES

[75] Inventors: Yukishige Ito, Tokyo, Japan; James C. Paulson, Del Mar, Calif.

[73] Assignee: Cytel, Inc., San Diego, Calif.

[21] Appl. No.: 57,528

[22] Filed: May 4, 1993

[51] Int. Cl.$^6$ .................. C12P 19/44; C12P 19/00; C12P 19/18; C12N 11/00

[52] U.S. Cl. ......................... 435/74; 435/72; 435/97; 435/101; 435/175; 435/193; 435/194

[58] Field of Search .................... 435/72, 74, 97, 101, 435/193, 194, 175

[56] References Cited

U.S. PATENT DOCUMENTS

| | | | |
|---|---|---|---|
| 4,918,009 | 4/1990 | Nilsson | 435/73 |
| 5,180,674 | 1/1993 | Roth | 435/97 |
| 5,246,840 | 9/1993 | Nilsson | 435/101 |

OTHER PUBLICATIONS

Schenkman et al "Cell" 65(7):1117–1125 (1991).
Baubichon-Cortay et al "Eur. J. Biochem" 182: 257–265 (1989).
Vendekerchoue et al "Glycobiology" 2(6) 541–8 (1992).
Schenkman et al "J. Exp Med" 175(2) 567–75 (1992).
Auge et al "Carbohydrate Res." 200 (1990)257–268.

Primary Examiner—Herbert J. Lilling
Attorney, Agent, or Firm—Welsh & Katz, Ltd.

[57] ABSTRACT

A single vessel cyclic synthesis process for preparation of a sialylα2→3βgalactoside is disclosed. In accordance with this process, a sialyltransferase acceptor is sialylated in an aqueous reaction medium by an α(2,3)sialyl transferase and CMP-sialic acid to form a sialyl donor substrate and CMP. In the presence of the trans-sialidase of *Trypanosoma crusi*, that sialyl donor substrate provides a sialyl group for a trans-sialidase acceptor, thereby preparing the sialylα2→3βgalactoside. The α(2,3)sialyltransferase acceptor is reformed upon trans-sialidation of the latter acceptor, and the sialyl donor substrate is reformed using the α(2,3)sialyltransferase and a CMP-sialic acid recycling system that combines CMP with sialic acid that is also present in the vessel. The $K_m/V_{max}$ value for the α(2,3)sialyltransferase acceptor is less than one-tenth the value of $K_m/V_{max}$ of the trans-sialidase acceptor for the α(2,3)sialyltransferase.

9 Claims, 2 Drawing Sheets

Scheme 1

Scheme 2

5,409,817

USE OF TRANS-SIALIDASE AND SIALYLTRANSFERASE FOR SYNTHESIS OF SIALYLα2→3βGALACTOSIDES

TECHNICAL FIELD

The present invention relates to the syntheses of sialylα2→3βgalactosides, and particularly to an enzymatic synthesis of such compounds in a single vessel using readily available starting materials.

BACKGROUND ART

The present invention is directed toward the synthesis of sialylα2→3βgalactoside compounds. Exemplary natural materials having the contemplated group are the gangliosides $G_{M3}$, $G_{M2}$, $G_{M1}$ and $G_{D1a}$, and the sialyl Lewis ligands, sialyl Lewis$^x$ and sialyl Lewis$^a$ as are present in leukocyte and non-leukocyte cell lines that bind to receptors such as the ELAM-1 and GMP 140 receptors. Polley et al., *Proc. Natl. Acad. Sci., USA*, 88:6224 (1991) and Phillips et al., *Science*, 250:1130 (1990).

A contemplated sialylα2→3βgalactoside can be prepared using well known organic chemical methods. Several sialylα2→3αgalactosides have also been prepared using enzymatic techniques. The organic chemical techniques are typically more cumbersome than the enzymatic techniques, requiring many protection and deprotection steps, whereas enzymatic techniques do not.

In the application of enzymes to the field of synthetic carbohydrate chemistry [(a) Toone et al., *Tetrahedron*, 45:5365 (1989); (b) David et al., *Adv. Carbohydr. Chem. Biochem*, 49:175 (1991); (c) Drueckhammer et al., *Synthesis*, 499 (1991); (d) Ichikawa et al., *Anal. Biochem.*, 202:215 (1992)], the use of sialyltransferase [(a) Sabesan et al, *J. Am. Chem. Soc.*, 108:2068 (1986); (b) Palcic et al., *Carbohydr. Res.*, 190:1 (1989); (c) Srivastava et al., *Carbohydr. Res.*, 207:259 (1990); (d) Palcic et al., *Glycobiology*, 1:205 (1990); (e) Pozsgay et al., *J. Org. Chem.*, 56:3377 (1991); (f) Ichikawa et al., *J. Am. Chem. Soc.*, 113:4698 (1991); (g) Ito et al., *J. Am. Chem. Soc.*, 115:1603 (1993)], for enzymatic sialylation is recognized to offer advantages over chemical methods [Reviews: (a) Okamoto et al., *Tetrahedron*, 46:5835 (1990); (b) Deninno, *Synthesis*, 583 (1991)], due to the virtually complete stereoselectivity and linkage specificity offered by the enzymes [Ito et al., *Pure Appl. Chem.*, 65:753 (1993)]. However, a major drawback of enzymatic of enzymatic sialylation in general is the rather strict acceptor substrate specificity of these enzymes that permits the synthesis of only a limited number of sialoside sequences.

A novel enzymatic process to introduce sialic acid (NeuAc) that addresses the above limitation and is widely applicable to the synthesis of glycan chains containing the terminal NeuAcα2→3Gal sequence such as sialyl Lewis $^x$ and its analogues that inhibit binding by the ELAM-1 and GMP-140 receptors is disclosed hereinafter.

BRIEF SUMMARY OF THE INVENTION

A process for forming a sialylα2→3βgalactoside is thus contemplated. That process comprises the steps of:
(a) combining the following components in a single vessel to form a reaction mixture:
(i) a catalytic amount of an α(2,3)sialyltransferase;
(ii) a catalytic amount of a CMP-sialic acid synthetase;
(iii) a catalytic amount of *Trypanosoma crusi* trans-sialidase;
(iv) a sialic acid;
(v) an oligosaccharide acceptor for the α(2,3)sialyltransferase having a β-linked galactosyl unit at the oligosaccharide non-reducing terminus;
(vi) an oligosaccharide acceptor for the trans-sialidase having a β-linked galactosyl unit at the oligosaccharide non-reducing terminus. This acceptor is free of fucosylation within two joined oligosaccharide units of the non-reducing terminal galactosyl unit;
the oligosaccharide acceptor of (v) having a $K_m/V_{max}$ value for the α(2,3)sialyltransferase that is less than one-tenth the $K_m/V_{max}$ of the oligosaccharide acceptor of (vi) for that same enzyme;
(vii) a CMP-sialic acid recycling system that comprises at least 2 moles of phosphoenolpyruvate per each mole of sialic acid, and catalytic amounts of ATP, myokinase, pyruvate kinase and inorganic pyrophosphatase; and
(viii) a buffered aqueous reaction medium containing enzymatically sufficient amounts of metal ion cofactors for said enzymes and having a pH value of about 6 to about 8;
the reaction mixture thus formed is maintained at a temperature of about zero degrees C. to about 45° C. for a time period sufficient for the trans-sialidase acceptor (vi) to be sialylated and form the desired sialylα(2→3)βgalactoside. The formed sialylα2→3βgalactoside is preferably recovered after formation.

Oligosaccharides are considered to have a reducing end and a non-reducing end, whether or not the saccharide at the reducing end is in fact a reducing sugar. In accordance with accepted nomenclature, oligosaccharides are depicted herein with the nonreducing end on the left and the reducing end on the right.

All oligosaccharides described herein are, thus, described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is a pyranose.

BRIEF DESCRIPTION OF THE DRAWINGS

In the drawings forming a part of this disclosure.

Figure 1:
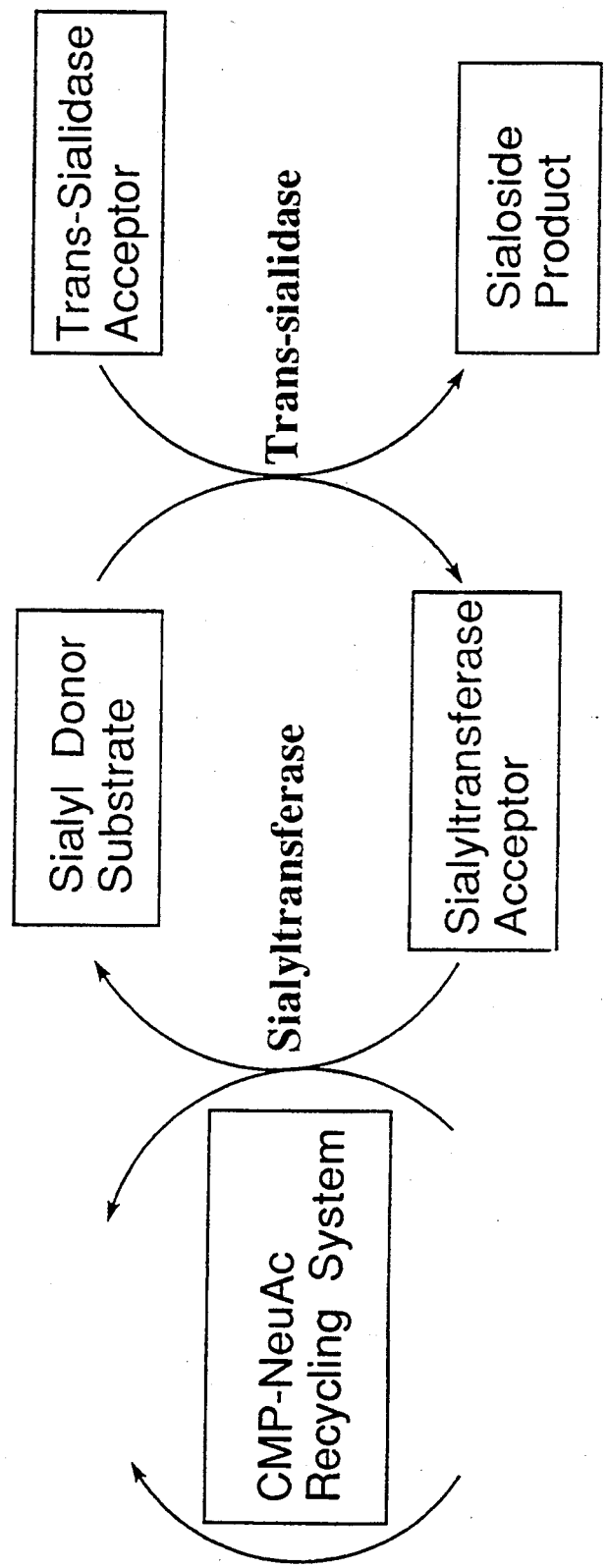
FIG. 1 shows a depiction as Scheme 1 of the coupled reactions utilized in the invention.
Figure 2:
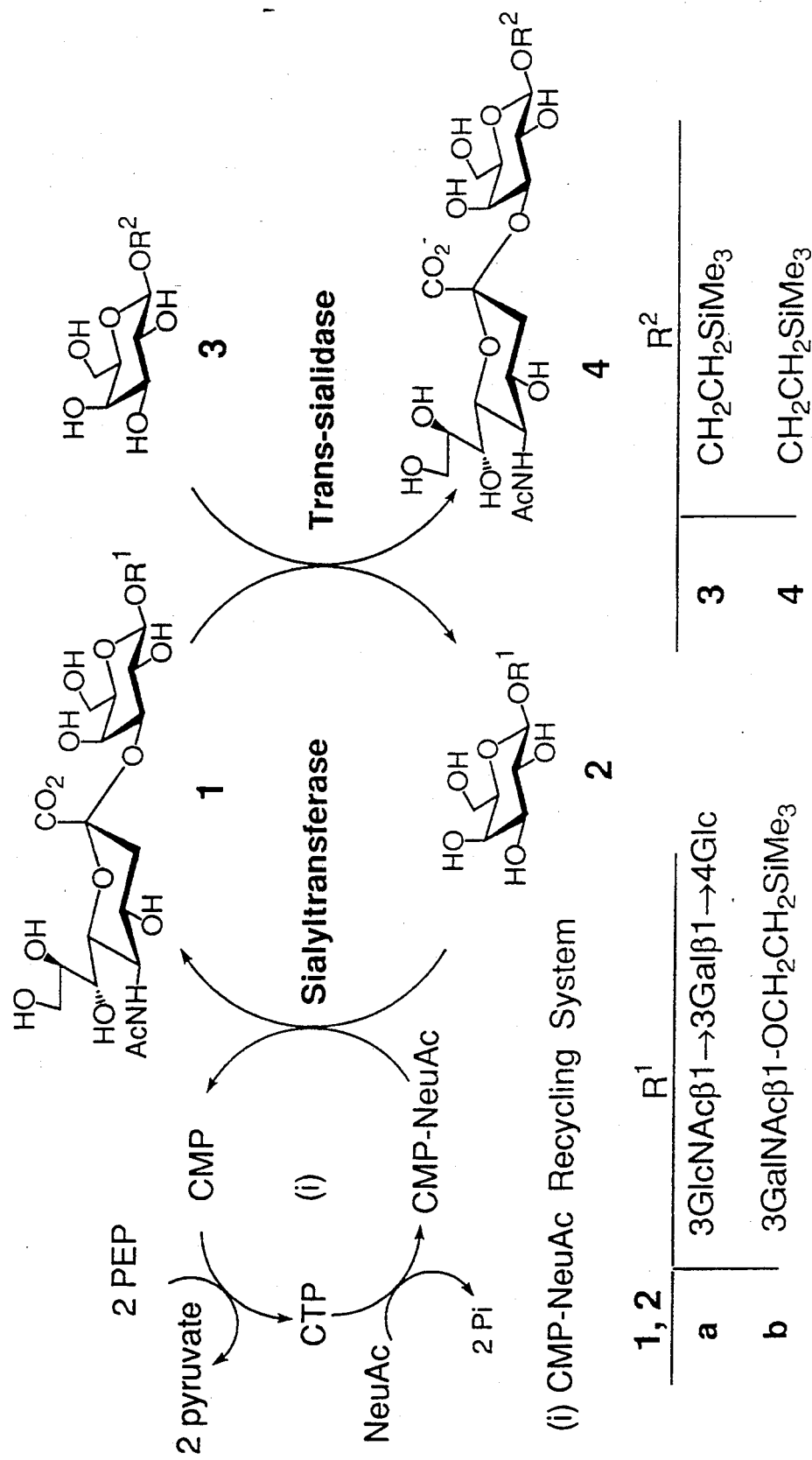
FIG. 2 shows a depiction as Scheme 2 of specifically coupled reactions utilized in the invention.

Abbreviations
Fru=fructosyl;
Fuc=fucosyl;
Gal=galactosyl;
GalNAc=N-acetylgalacto;
Glc=glucosyl;
GlcNAc=N-acetylgluco;
Man=mannosyl;
ManNAc=N-acetylmannosyl; and
NeuAc=sialyl (N-acetylneuraminyl).

DETAILED DESCRIPTION OF THE INVENTION reactions illustrated generally in Scheme 1, below, and more specifically in Scheme 2, thereafter.

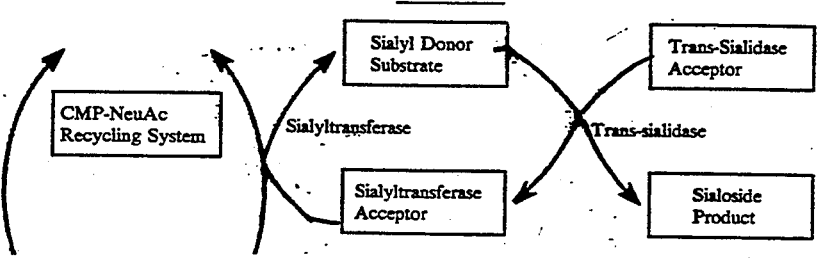

FIG. 1

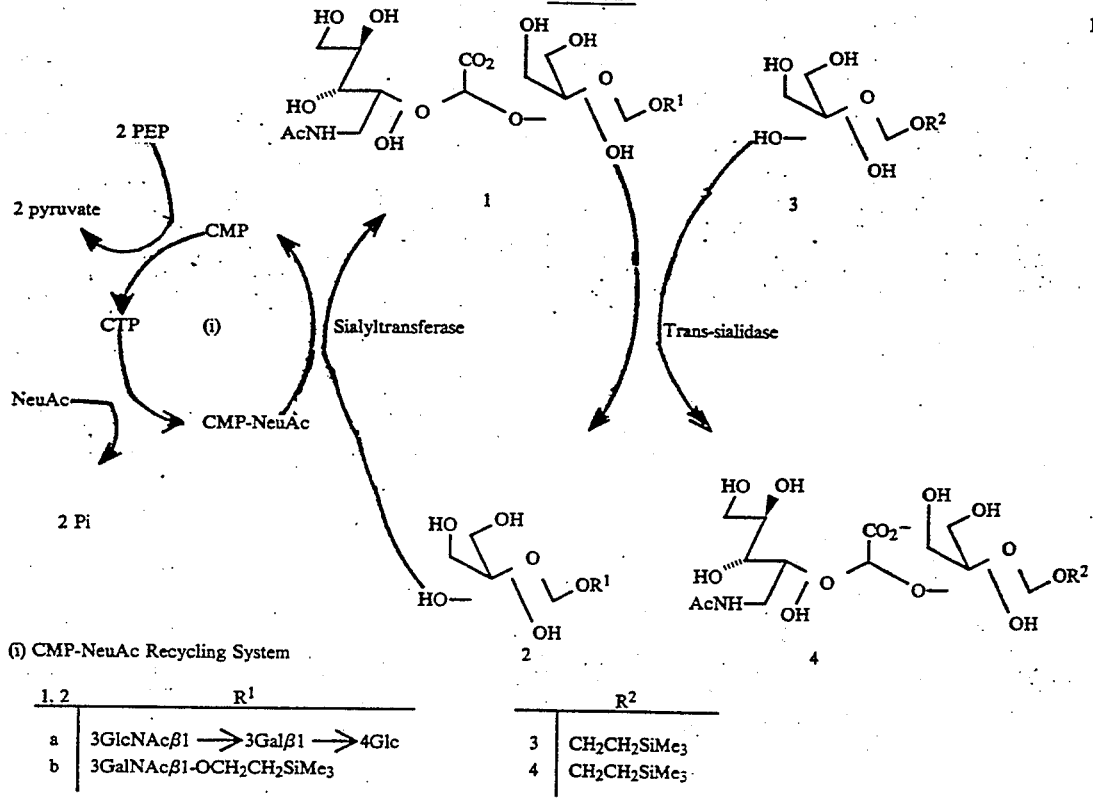

FIG. 2

(i) CMP-NeuAc Recycling System

| 1, 2 | $R^1$ | | $R^2$ |
|---|---|---|---|
| a | 3GlcNAcβ1 →3Galβ1 →4Glc | 3 | $CH_2CH_2SiMe_3$ |
| b | 3GalNAcβ1-OCH$_2$CH$_2$SiMe$_3$ | 4 | $CH_2CH_2SiMe_3$ |

A. Introduction

A process of this invention takes advantage of a newly described trans-sialidase enzyme from *Trypanosoma crusi* [Schenkman et al., *Cell*, 65:1117 (1991)], that has the unique property of catalyzing the reversible transfer of NeuAc from a donor substrate of the sequence NeuAcα2→3βGal-O-$R^1$, wherein $R^1$ is a first $R^2$ is a second β-linked group different from $R^1$, to yield a new product NeuAcα2→3Gal-O-$R^2$. Vandekerckhove et al., *Glycobiology*, 6:541 (1992).

The primary limitation in the use of this enzyme for synthetic purposes is that the desired product is produced at the expense of another sialoside used as the donor substrate. In addition, because the transfer of NeuAc is a reversible process, it is difficult to drive the equilibrium in favor of the desired sialoside (NeuAcα2→3βGal-O-$R^2$).

The limitation in the use of a trans-sialidase has been overcome as has the difficulty in driving the reaction to favor the desired sialoside as is shown by the coupled Thus, an available relatively inexpensive sialyl donor substrate such as Compound 1 provides the sialyl group to a trans-sialidase acceptor such as Compound 3 to form the sialoside product, Compound 4. After transfer of its sialyl group to form sialyltransferase acceptor, Compound 2, Compound 1 is regenerated using an α(2,3)sialyltransferase to transfer free sialic acid via the catalytic in situ regeneration of CMP-sialic acid according to Ichikawa et al., *J. Am. Chem. Soc.*, 113:4698 (1991). The stoichiometric substrates of this enzymatic system are free sialic acid, phosphoenolpyruvate (PEP), and the galactoside acceptor substrate utilized by the trans-sialidase as is discussed hereinafter.

B. The Process

A contemplated process is carried out in a single reaction vessel and such a process is often referred to in the art as a "one pot" process. As such, all of the reagents, including the enzymes, and starting chemicals are admixed together at substantially the same time and in a single aqueous reaction medium.

A process for forming a sialylα2→3βgalactoside (sialoside product) is thus contemplated. That process comprises the steps of:
(a) combining the following components in a single vessel to form a reaction mixture:
  (i) a catalytic amount of an α(2,3)sialyltransferase;
  (ii) a catalytic amount of a CMP-sialic acid synthetase;
  (iii) a catalytic amount of Trypanosoma crusi trans-sialidase;
  (iv) a sialic acid;
  (v) an oligosaccharide acceptor for the α(2,3)sialyltransferase having a β-linked galactosyl unit at the oligosaccharide non-reducing terminus;
  (vi) an oligosaccharide acceptor for the trans-sialidase having a β-linked galactosyl unit at the oligosaccharide non-reducing terminus. This acceptor is free of fucosylation within two joined oligosaccharide units of the non-reducing terminal galactosyl unit;
  the oligosaccharide acceptor of (v) having a $K_m/V_{max}$ value for the α(2,3)sialyltransferase that is less than one-tenth the $K_m/V_{max}$ of the oligosaccharide acceptor of (vi) for that same enzyme;
  (vii) a CMP-sialylic acid recycling system that comprises at least 2 moles of phosphoenolpyruvate per each mole of sialylic acid, and catalytic amounts of ATP, myokinase, pyruvate kinase and inorganic pyrophosphatase; and
  (viii) a buffered aqueous reaction medium containing enzymatically sufficient amounts of metal ion cofactors for said enzymes and having a pH value of about 6 to about 8.

The reaction mixture thus formed is maintained at a temperature of about zero degrees C. to about 45° C. for a time period sufficient for the acceptor (vi) to be sialylated and form the desired sialylα2→3βgalactoside (sialoside product of Scheme 1). The formed sialylα2→3βgalactoside is preferably recovered after formation.

An α(2,3)sialyltransferase, often referred to as the sialyltransferase, is one of the three principal enzymes utilized herein. This enzyme transfers sialic acid to a β-linked Gal with the formation of an α-linkage between the two saccharides. Bonding (linkage) between the saccharides is between the 2-position of NeuAc and the 3-position of Gal.

An exemplary α(2,3) sialyltransferase referred to as α(2,3)sialtransferase (EC 2.4.99.6) transfers sialic acid to the non-reducing terminal Gal of a Galβ1→3GlcNAc or Galβ1→4GlcNAc disaccharide or glycoside [Van den Eijnden et al., J. Biol. Chem., 256:3159 (1981); Weinstein et al., J. Biol. Chem., 257:13845 (1982); Wen et al., J. Biol. Chem., 267:21011 (1992)]. Another exemplary α-2,3-sialyltransferase (EC 2.4.99.4) transfers sialic acid to the non-reducing terminal Gal of a Galβ1→3GalNAc disaccharide or glycoside [Rearick et al., J. Biol. Chem., 254:4444 (1979); Gillespie et al., J. Biol. Chem., 267:21004 (1992)].

CMP-Sialic acid synthetase is an enzyme that is utilized in the CMP-sialic acid regenerating system that is discussed in detail hereinafter. For example, CMP-sialic acid synthetase can be isolated and purified from cells and tissues containing the synthetase enzyme by procedures well known in the art. See, e.g., Gross et al., Eur. J. Biochem., 168:595 (1987); Vijay et al., J. Biol. Chem., 250(1) 164 (1975); Zapata et al., J. Biol. Chem., 264(25):14769 (1989) and Higa et al., J. Biol. Chem., 260(15):8838 (1985). The gene for this enzyme has also been sequenced. Vann et al., J. Biol. Chem., 262:17556 (1987). Shames et al. also recently reported overexpression of the gene for use in a gram scale synthesis of CMP-NeuAc. Glycobiology, 1:187 (1991). This enzyme is also commercially available.

The third principal enzyme used here is the trans-sialidase of Trypanosoma crusi (T. crusi) whose isolation and reactivity was reported in Vendekerckhove et al., Glycobiology, 6:541 (1992). This enzyme is often referred to as the trans-sialidase, and has a broad specificity for transferring sialic acid from a wide variety of NeuAcα2→3βGal-containing donor oligosaccharides to the non-reducing terminus (end) of a narrower range oligosaccharide acceptors whose nonreducing terminal saccharide is a β-linked Gal. A sialic acid is not transferred from an α(2,6)-linked Gal.

A sialic acid is also required. As noted previously, the use of a sialic acid to regenerate the sialyl donor of Schemes 1 and 2 drives the trans-sialidase-catalyzed equilibrium reaction toward making the desired sialylated product.

A contemplated sialic acid includes not only sialic acid itself (5-N-acetylneuraminic acid; 5-N-acetylamino-3,5-dideoxy-D-glycero-D-galacto-2-nonulosonic acid; NeuAc, and sometimes also abbreviated AcNeu or NANA), but also 9-substituted sialic acids such as a 9-0-$C_1$-$C_6$ acyl-NeuAc like 9-0-lactyl-NeuAc or 9-0-acetyl-NeuAc, 9-deoxy-9-fluoro-NeuAc and 9-azido-9-deoxy NeuAc. Use of sialic acid analogs having changes at other positions impairs the activity of one or more of the enzymes utilized herein. The synthesis and use of these compounds in a silylation procedure is disclosed in international application WO 92/16640, published Oct. 1, 1992.

Two acceptor oligosaccharides are also used; (a) one for the α(2,3)sialyltransferase, which after sialylation becomes the sialyl donor, and (b) one for the T. Crusi trans-sialidase. These two acceptor molecules are chosen so that each is a substrate for one of the sialyltransferase or the trans-sialidase, but is substantially not a substrate for the other enzyme either by structure or by its use in a catalytic amount.

Thus, using the α(2,3)sialyltransferase acceptors of Scheme 2 (Compounds 2a and 2b) as exemplary and keeping in mind the before-discussed structural preferences and requirements of the T. crusi trans-sialidase for an acceptor substrate, it is seen that Compound 2a that has a non-reducing terminal Galβ1→3GlcNAc linkage, whereas Compound 2b contains a Galβ1→3GalNAc linkage, neither of which is preferred for an acceptor for the trans-sialidase, and both are present in a catalytic amount. Both compounds can be acceptors for the trans-sialidase, but are relatively poor acceptors, and by adjusting the concentration of those compounds relative to a preferred trans-sialidase acceptor substrate, the trans-sialidation reaction of the sialytransferase acceptor can be minimized, if not eliminated.

Similarly, using the trans-sialidase acceptor of Scheme 2 (Compound 3) as exemplary, it is seen that that acceptor does not contain the non-reducing terminal Galβ1→3/4GlcNAc or Galβ1→3GalNAc utilized by an exemplary sialyltransferase. The trans-sialidase acceptor substrates are therefore not acceptor substrates for the α(2,3)sialyltransferase.

A structural limitation for the αGal-terminated trans-sialidase acceptor substrate is that there not be a Fuc within two linked saccharides of that non-reducing terminal Gal. Another somewhat less important structural limitation for this acceptor is that the non-reducing two terminal saccharides be other than Galβ1→3GlcNAc or Galβ1→3GalNAc, as both structures are relatively good acceptors at higher concentrations, e.g. about 10 mM. The length of the acceptor is not important.

The structures of the two non-reducing terminal saccharide units of both the sialyltransferase acceptor and the trans-sialidase acceptor are governed by the reactivity of both with the sialyltransferase. That is, if the trans-sialidase acceptor were a good substrate for the sialyltransferase, this process would not be needed, and a worker would simply use the sialyltransferase to make the desired sialoside. Thus, the trans-sialidase acceptor should at best be a poor substrate for the sialyltransferase, whereas the sialyltransferase acceptor should be a good substrate for that enzyme.

One way to quantify how good a substrate is for an enzyme is to determine the value of $K_m/V_{max}$ for that substrate and that enzyme. $K_m$ is the Michaelis constant in units of moles/liter. $V_{max}$ is the maximum reaction velocity at a constant concentration of enzyme, and is in units of enzyme unit/milligram, one enzyme unit being that amount of enzyme that will catalyze the transformation of one micromole of substrate per minute under optimal conditions. The value of $K_m/V_{max}$ is the slope of the line obtained from a Lineweaver-Burk plot.

The value of $K_m/V_{max}$ for the sialyltransferase acceptor is less than one-tenth, more preferably less than one-twentieth, and most preferably less than one-hundredth, that of the $K_m/V_{max}$ value of the trans-sialidase acceptor for that same enzyme. Thus, because both the sialyltransferase acceptor and trans-sialidase acceptor are present in the same vessel at the same time, and the former can be present at a higher concentration, it is possible that the trans-sialidase acceptor could be sialylated in preference to the sialyltransferase acceptor. Selection of appropriate acceptor substrates for both enzymes and their concentrations, coupled with selection of an appropriate α-sialylating enzyme help to assure that the desired sialylated product is prepared.

Values for $K_m$ and $V_{max}$ for α(2,3)sialyltransferase catalyzed transfers to many sialyltransferase acceptor galactosyl glycosides are available in the published literature and can be obtained using well known enzymatic techniques. Exemplary values for several such acceptor galactosyl glycosides are listed below in Table 1 whose data are taken from Rearick et al., *J. Biol. Chem.*, 254:4444 (1979), Beyer et al., *Adv. Enzymol.*, 52:23-175 (1981) and Weinstein et al., *J. Biol. Chem.*, 257:13845 (1982), wherein those compounds are referred to as "acceptors" for the α-sialyltransferase.

TABLE 1

$K_m$ and $V_{max}$ Values for Acceptor Molecules and α-Sialyltransferases

| α-(2,3)Sialyl transferase | Acceptor | $K_m$ (mM) | $V_{max}$ (units/ mg) | $K_m/V_{max}$ mM-units mg |
|---|---|---|---|---|
| EC 2.4.99.4 | Galβ1→3GalNAc | 0.21 | 8.9 | 0.024 |
| | lacto-N-tetraose[1] | 27 | 3.6 | 7.5 |
| | Galβ1→3GlcNAc | 65 | 4.4 | 15 |
| | Galβ1→6GlcNAc | 29 | 0.24 | 121 |
| | Galβ1→4Glc | 180 | 0.62 | 290 |
| | Galβ1→4GlcNAc | 42 | 0.11 | 382 |
| | Galβ1→OCH3[2] | — | — | >100 |
| | lacto-N-neo-tetraose[2,3] | — | — | >100 |
| EC 2.4.99.6 | lacto-N-tetraose[1] | 0.09 | 1.00 | 0.09 |
| | Galβ1→3GlcNAc | 0.64 | 1.16 | 0.55 |
| | Galβ1→4GlcNAc | 2.7 | 0.75 | 3.6 |
| | lacto-N-neo-tetraose[3] | 4.22 | 0.98 | 4.3 |
| | Galβ1→4Glc | 9.4 | 0.91 | 10 |
| | Galβ1→3GalNAc[4] | — | — | >10 |

[1]Lacto-N-tetraose = Galβ1→3GlcNAcβ1→3Galβ1→4Glc.
[2]Value approximated from the data in Rearick et al., J. Biol. Chem., 254:4444 (1979).
[3]Lacto-N-neo-tetraose = Galβ1→4GlcNAcβ1→3Galβ1→4Glc.
[4]Value approximated from the data in Weinstein et al., J. Biol. Chem., 257:13845 (1982).

With the understanding that it is substantially only the two-non-reducing-terminal saccharides and their substituents that determine the specificity of the α(2,3-)sialyltransferase and trans-sialidase, the absence of a fucosyl group within two saccharide units of the non-reducing terminus for the trans-sialidase and the appropriate pairing of the two acceptors using $K_m/V_{max}$ values or similar data as discussed herein, further exemplary non-reducing terminal structures for trans-sialidase acceptors for each of the enzymes are illustrated below in Table 2.

Table 2

Non-Reducing Terminal Structures for Trans-Sialidase Acceptor Saccharides

Trans-Sialidase Acceptor Terminal Structure

Galβ1→4Fru
Galβ1→4Gluconic acid
Galβ1→4Man
Galβ1→4Glc
Galβ1→3arabinose
Galβ1→3Gal
Galβ1→6Gal
Galβ1→6GlcNAc
galactose
α-methyl-galactose
β-methyl-galactose Thus, a relatively inexpensive sialyl donor such as lacto-N-tetraose used here or ganglioside $G_{M1}$ or $G_{D1a}$ can be used along with an appropriate α(2,3)sialyltransferase and CMP-NeuAc recycling system to prepare a more difficultly prepared sialylated product via the trans-sialidase when the various reactions are coupled in a single reaction vessel.

It is to be understood that a useful trans-sialidase acceptor substrate may not be bound by the sialyltransferase or be bound very poorly, and if bound may not be sialylated or be sialylated very slowly. The $K_m/V_{max}$ value for that compound and the sialyltransferase acceptor can therefore be very large and the difference can be almost infinite.

The CMP-sialic acid recycling system utilizes CMP-sialic acid synthetase as noted previously. As shown in Schemes 1 and 2, CMP-sialic acid (shown in Scheme 2 as CMP-NeuAc) reacts with a sialyltransferase acceptor in the presence of a α(2,3)sialyltransferase (shown in the schemes as sialyltransferase) to form the sialyl donor substrate of Scheme 1, e.g., Compound 1 of Scheme 2. It is this reformation and use of the sialyl donor substrate that drives the conversion of trans-sialidase acceptor, e.g., Compound 3, toward complete formation of the desired sialoside product, e.g., Compound 4.

The CMP-sialic acid regenerating system used in the present invention comprises cytidine monophosphate (CMP), a nucleoside triphosphate, a phosphate donor, a kinase capable of transferring phosphate from the phosphate donor to nucleoside diphosphates and a nucleoside monophosphate kinase capable of transferring the terminal phosphate from a nucleoside triphosphate to CMP. The previously discussed α(2,3)sialyltransferase and CMP-sialic acid synthetase can also be formally viewed as part of the CMP-sialic acid regenerating system. However, because those two enzymes have already been discussed, they will not be discussed further here.

Nucleoside triphosphates suitable for use in accordance with the CMP-sialic acid regenerating system are adenosine triphosphate (ATP), cytidine triphosphate (CTP), uridine triphosphate (UTP), guanosine triphosphate (GTP), inosine triphosphate (ITP) and thymidine triphosphate (TTP). A preferred nucleoside triphosphate is ATP.

Nucleoside monophosphate kinases are enzymes that catalyze the phosphorylation of nucleoside monophosphates. Nucleoside monophosphate kinase (NMK) or myokinase (MK; EC 2.7.4.3) used in accordance with the CMP-sialic acid regenerating system of the present invention are used to catalyze the phosphorylation of CMP. NMK's are commercially available (Sigma Chem. Co., St. Louis, Mo.; Boehringer Mannheim, Indianapolis, Ind.).

A phosphate donor and a catalytic amount of a kinase that catalyzes the transfer of phosphate from the phosphate donor to an activating nucleotide are also part of the CMP-sialic acid regenerating system. The phosphate donor of the regenerating system is a phosphorylated compound, the phosphate group of which can be used to phosphorylate the nucleoside phosphate. The only limitation on the selection of a phosphate donor is that neither the phosphorylated nor the dephosphorylated forms of the phosphate donor can substantially interfere with any of the reactions involved in the formation of the sialylated acceptor saccharide. Preferred phosphate donors are phosphoenolpyruvate (PEP) and acetyl phosphate. A particularly preferred phosphate donor is PEP.

The selection of a particular kinase for use in accordance with the present invention depends upon the phosphate donor employed. When acetyl phosphate is used as the phosphate donor, the kinase is acetyl kinase. When PEP is used as the phosphate donor, the kinase is pyruvate kinase (PK; EC 2.7.1.40). Other kinases can be employed with other phosphate donors as is well known to those of skill in the art. Kinases are commercially available (Sigma Chem. Co., St. Louis, Mo.; Boehringer Mannheim, Indianapolis, Ind.).

Because of the self-contained and cyclic character of this glycosylation method, once all the reactants and enzymes are present, the reaction continues until the first of the stoichiometric substrates (free NeuAc, PEP or trans-sialidase acceptor) is consumed.

Thus, in the sialylation example, CMP is converted to CDP, whose conversion is catalyzed by nucleoside monophosphate kinase or myokinase in the presence of added ATP. ATP is catalytically regenerated from its byproduct, ADP, by pyruvate kinase (PK) in the presence of added phosphoenolpyruvate (PEP). CDP is further converted to CTP, which conversion is catalyzed by PK in the presence of PEP. CTP reacts with sialic acid to form inorganic pyrophosphate (PPi) and CMP-sialic acid, the latter reaction being catalyzed by CMP-sialic acid synthetase. Following sialylation of the α(2,3)sialyltransferase acceptor compound, the released CMP re-enters the regenerating system to reform CDP, CTP and CMP-sialic acid. The formed PPi is scavenged as discussed below, and forms inorganic phosphate (Pi) as a byproduct. Pyruvate is also a byproduct.

The byproduct pyruvate can also be made use of in another reaction in which N-acetylmannosamine (ManNAc) and pyruvate are reacted in the presence of NeuAc aldolase (EC 4.1.3.3) to form sialic acid. Thus, the sialic acid can be replaced by ManNAc and a catalytic amount of NeuAc aldolase. Although NeuAc aldolase also catalyzes the reverse reaction (NeuAc to ManNAc and pyruvate), the produced NeuAc is irreversibly incorporated into the reaction cycle via CMP-NeuAc catalyzed by CMP-sialic acid synthetase coupled with inorganic pyrophosphatase (PPase)-catalyzed decomposition of the released inorganic pyrophosphate. This enzymatic synthesis of sialic acid and its 9-substituted derivatives and the use of a resulting sialic acid in a different sialylating reaction scheme is disclosed in International application WO 92/16640, published on Oct. 1, 1992.

As used herein, the term "pyrophosphate scavenger" refers to substances that serve to remove inorganic pyrophosphate from a reaction mixture of the present invention. Inorganic pyrophosphate (PPi) is a byproduct of the preparation of CMP-NeuAc.

Produced PPi can feed back to inhibit other enzymes such that glycosylation is reduced. However, PPi can be degraded enzymatically or by physical means such as sequestration by a PPi binding substance. Preferably, PPi is removed by hydrolysis using inorganic pyrophosphatase (PPase; EC 3.6.1.1), a commercially available PPi catabolic enzyme (Sigma Chem. Co., St. Louis, Mo.; Boehringer Mannheim, Indianapolis, Ind.), and that or a similar enzyme serves as the pyrophosphate scavenger.

The concentrations or amounts of the various reactants used in this trans-sialylation process depend upon numerous factors including reaction conditions such as temperature and pH value, and the choice and amount of acceptor saccharides to be sialylated. Because this sialylation process permits regeneration of activating nucleotides, activated donor sialic acid and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, acceptor saccharide and enzymes are selected such that trans-sialylation proceeds until the sialic acid is consumed.

By way of example, when the concentration of sialic acid is about 10.5 mM, preferred concentrations of the other non-enzyme reactants are about 1.0 mM for the α(2,3)sialyltransferase acceptor compound, about 10.5 mM for the trans-sialidase acceptor, about 0.9 mM for CMP, about 0.09 mM for the nucleoside triphosphate (ATP) and about 46 mM for the phosphate donor (PEP). Thus, the ratio of the concentration of the three saccharides used illustratively here; i.e., sialic acid:α(2,3)sialyltransferase acceptor:trans-sialidase acceptor, is about 10:1:10. Lower limits for those molar ratios can be about 1:0.001:1, and more preferably, about 1:0.01:1, in the order mentioned. Stated together, those ratios are about 1:0.001–1:1. The CMP is present in about an equal amount to the α(2,3)sialyltransferase acceptor, and ATP is present at about one-tenth the amount of CMP. Where the sialic acid is prepared in situ from ManNAc, as discussed before, the relative amount of the sialic acid can be based on the ManNAc utilized.

Each of the enzymes is present in a catalytic amount. As used herein, the phrase "catalytic amount" means that amount of an enzyme at least sufficient to catalyze, in a non-rate limiting manner, the conversion of that enzyme's substrate to product.

The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

It is to be remembered that the α(2,3)sialyltransferase acceptor is recycled in a contemplated process. As a consequence of that fact, one may start a reaction with either that acceptor, its sialylated donor or some of each molecule. Thus, the above ratio is for the total concentration of acceptor and sialylated donor. The choice of which to use is mostly a question of cost and availability, with the least expensive, most available reagent typically being the reagent of choice. Here, exemplary Compounds 1a and 1b of Scheme 2 fit that description and were used.

Similarly cycled are CMP/CTP and NeuAc/CMP-NeuAc. One can therefore begin the reaction with either or both of CMP and CTP, as well as with either or both of NeuAc and CMP-NeuAc. Inasmuch as CMP and NeuAc are the less expensive and most readily available of those pairs, those reagents are used to start the reaction, with the amounts discussed before being those for the total amount of each pair used. Of course, one can also start with CMP and ManNAc, along with NeuAc aldolase, as discussed before.

The above ingredients are combined by admixture in a buffered aqueous reaction medium (solution). That buffered medium has a pH value of about 6 to about 8. The buffer is devoid of chelators that bind enzyme cofactors such as $Mg^{+2}$ or $Mn^{+2}$. The selection of a buffer is based on the ability of the buffer to maintain pH value at the desired level. Where the pH value is about 7.5, a preferred buffer is HEPES.

The reaction medium is also preferably free of solubilizing detergents and organic solvents such as methanol or ethanol. In addition, the enzymes are preferably utilized free in solution as compared to being bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about zero degrees C. to about 45° C., and more preferably at about 20° C. to about 30° C.

The reaction mixture so formed is maintained for a period of time sufficient for the trans-sialidase acceptor to be sialylated to form a desired sialylα2→3βgalactoside (sialoside) product. Some of that product can often be detected after a few hours, with recoverable amounts usually being obtained within 24 hours. It is preferred to optimize the yield of the process, and the maintenance time is usually about 36 to about 120 hours.

The produced sialylα2→3βgalactoside can be used without purification. However, it is usually preferred to recover the product. Standard, well known techniques for recovery of sialylated saccharides such as thin or thick layer chromatography, ion exchange chromatography can be used. It is preferred to use one or more column chromatographic techniques for the recovery as is discussed hereinafter and in the literature cited herein.

Results

As an example of this reaction, the simple sialoside Compound 4 was prepared, which represents the oligosaccharide moiety of ganglioside $G_{M4}$. This simple target compound was chosen to illustrate the utility of this system for two reasons.

First, the corresponding galactoside Compound 3 [Jansson et al., *J. Org. Chem.*, 53:5629 (1988)] is a poor substrate of all known α(2,3)sialyltransferases and cannot be efficiently sialylated using these enzymes. Second, after protection of hydroxy and carboxylate groups and selective cleavage of 2-(trimethylsilyl)ethyl glycoside, the sialoside Compound 4 is readily converted to a disaccharide glycosyl donor that can be used in the block chemical synthesis of ganglioside $G_{M4}$ and more complex sialosides [(a) Suguimoto et al., *Tetrahedron Lett.*, 31:385 (1990); (b) Kameyama et al., *Carbohydr. Res.*, 209 (1991)] as reported by others.

The reaction was performed as follows. A mixture of Compound 3 (10.5 μmol), NeuAc (10.5 μmol), lacto-N-tetraose (Compound 1a; 1.0 μmol; Sigma Chemical Co., St. Louis Mo.), CMP (0.9 μmol), ATP (0.09 μmol), phosphoenolpyruvate trisodium salt (46 μmol), $MgCl_2$ (10.5 μmol), $MnCl_2$ (3 μmol), KCl (10.5 μmol), BSA (5 percent; 5 μl), mercaptoethanol (0.03 μl), myokinase (EC 2.7.4.3; 15 U), pyruvate kinase (EC 2.7.1.40; 25 U), inorganic pyrophosphatase (EC 3.6.1.1; 1.6 U), αGal1,3/4GlcNAc α(2,3)sialyltransferase [EC 2.4.99.6; Wen et al., *J. Biol. Chem.*, 267:21011 (1992)] (16 mU), *Trypanosoma crusi* trans-sialidase (7 mU), and CMP-NeuAc synthetase [(a) Vann et al., *J. Biol. Chem.*, 262:17556 (1987); (b) Shames et al., *Glycobiology*, 1:187 (1991)] (80 mU) in 200 mM HEPES buffer (pH 7.4; 1.0 ml) was incubated at room temperature for four days. The mixture was passed through Sep-Pack $C_{18}$ cartridge (Waters). Trans-sialidase was a gift from Dr. Victor Nussenzweig, Department of Pathology, New York University Medical Center. One trans-sialidase Unit (U) refers to the amount of enzyme that sialylates 1 μmole of lactose/minute at room temperature, pH 7 (0.1 mM lactose and 1 mM sialylα2→3lactose).

The cartridge was washed with 0.1M $NH_4HCO_3$ and eluted with 50 percent MeOH. Fractions containing the product were collected and purified by a column of Bio-Gel P2 (0.1M $NH_4HCO_3$) to afford Compound 4. (3.9 mg, 65 percent).

The same transformation could be achieved in a comparable efficiency by using a different sialyltransferase [Galβ1→3GalNAcα(2,3)sialyltransferase; Gillespie et al., *J. Biol. Chem.*, 267:21004 (1992); EC 2.4.99.4] and it's preferred galactoside acceptor Compound 1b.

Fucosylation of Compound 4 or a similar product provides an analogue of sialyl Lewis$_x$ that can inhibit binding to ELAM-1 or GMP-140. That fucosylation is preferably carried out enzymatically as discussed in Ichikawa et al., *J. Am. Chem. Soc.*, 114:9283 (1992).

The results demonstrate the synthetic potential of the *T. crusi* trans-sialidase. The multienzyme system can be viewed as an extension of the acceptor substrate specificity of sialyltransferases. Due to the broad specificity of the trans-sialidase, many naturally occurring NeuA-cα2→3Gal-OR$^2$ sequences can be synthesized by substituting different galactoside acceptor substrate. The other advantage of this multienzyme system is that the equilibrium of the trans-sialidase is shifted toward product formation by the sialyltransferase cycle. Because large scale preparation of both sialyltransferase and CMP-NeuAc synthetase are now possible [Ichikawa et al., *J. Am. Chem. Soc.*, 114:9283 (1992)], further improvement of efficiency should be possible, once larger scale preparation of a recombinant trans-sialidase is established.

The $^1$H and $^{13}$C NMR data for Compound 4 are provided below:

$^1$H NMR (D$_2$O, 300 MHz) δ4.44 (d, J 7 Hz, H-1Gal), 4.04 (dd, J 10 and 3 Hz, H-3Gal), 3.91 (d, J 3 Hz, H-4Gal), 3.48 (dd, J 10 and 7 Hz, H-2Gal), 2.72 (dd, J 12 and 4 Hz, H-3eqNeuAc), 2.00 (s, NAc), 1.77 (t, J 12 Hz, H-3axNeuAc). $^{13}$C NMR (D$_2$O, 75 MHz) δ175.4, 174.3, 102.3 (C-1Gal), 100.3 (C-2NeuAc), 76.4 (C-3Gal), 75.3, 73.3, 72.2, 69.5, 68.8, 68.7, 68.5, 67.9, 63.0, 61.3, 52.1 (C-5NeuAc), 40.1, 22.5 (COCH$_3$), 18.0 (CH$_2$SiMe$_3$), −2.1 (SiMe$_3$).

The foregoing is intended as illustrative of the present invention but not limiting. Numerous variations and modifications may be effected without departing from the true spirit and scope of the novel concepts of the invention.

We claim:

1. A process for forming a sialylα2→3βgalactoside that comprises the steps of:
   combining the following components in a single vessel to form a reaction mixture:
   (i) a catalytic amount of an α(2,3)sialyltransferase;
   (ii) a catalytic amount of a CMP-sialic acid synthetase;
   (iii) a catalytic amount of *Trypanosoma crusi* trans-sialidase;
   (iv) a sialic acid;
   (v) an oligosaccharide acceptor for said α(2,3-)sialyltransferase having a β-linked galactosyl unit at the oligosaccharide non-reducing terminus;
   (vi) an oligosaccharide acceptor for said trans-sialidase having a β-linked galactosyl unit at the oligosaccharide non-reducing terminus, said acceptor being free of fucosylation within two joined oligosaccharide units of said non-reducing terminal galactosyl unit;
   said oligosaccharide acceptor of (v) having a $K_m/V_{max}$ value for said α(2,3)sialyltransferase that is less than one-tenth said $K_m/V_{max}$ of said oligosaccharide acceptor of (vi) for that same enzyme;
   (vii) a CMP-sialic acid recycling system that comprises at least 2 moles of phosphoenolpyruvate per each mole of sialic acid, and catalytic amounts of ATP, myokinase, pyruvate kinase and inorganic pyrophosphatase; and
   (viii) a buffered aqueous reaction medium containing enzymatically sufficient amounts of metal ion cofactors for said enzymes and having a pH value of about 6 to about 8;
   maintaining said reaction mixture at a temperature of about zero degrees C. to about 45° C. for a time period sufficient for said acceptor (vi) to be sialylated and form said sialylα2→3βgalactoside.

2. The process according to claim 1 including the further step of recovering said formed sialylα2→3β-galactoside.

3. The process according to claim 1 wherein said acceptor of (vi) is 2-(trimethylsilyl)ethyl-β-galactoside.

4. The process according to claim 1 wherein said acceptor of (v) is lacto-N-tetraose.

5. The process according to claim 1 wherein said acceptor of (vi) is Galβ1→3GalNAc1—OCH$_2$CH$_2$SiMe$_3$.

6. The process according to claim 1 wherein said oligosaccharide acceptor of (v) has a $K_m/V_{max}$ that is less than one-tenth of the $K_m/V_{max}$ value of said oligosaccharide acceptor of (vi) for said α(2,3) sialyltransferase.

7. The process according to claim 1 wherein said sialic acid is 5-N-acetylneuraminic acid.

8. A process for forming a sialylα2→3βgalactoside that comprises the steps of:
   combining the following compoents in a single vessel to form a reaction mixture:
   (i) a catalytic amount of an α(2,3)sialyltransferase;
   (ii) a catalytic amount of a CMP-sialic acid synthetase;
   (iii) a catalytic amount of *Trypanosoma crusi* trans-sialidase;
   (iv) sialic acid;
   (v) lacto-N-tetraose;
   (vi) an oligosaccharide acceptor for said trans-sialidase having a β-linked galactosyl unit at the oligosaccharide non-reducing terminus, said acceptor being free of fucosylation within two joined oligosaccharide units of said non-reducing terminal galactosyl unit;
   said oligosaccharide acceptor of (v) having a $K_m/V_{max}$ value for said α(2,3)sialyltransferase that is less than one-tenth said $K_m/V_{max}$ of said oligosaccharide acceptor of (vi) for that same enzyme;
   (vii) a CMP-sialylic acid recycling system that comprises at least 2 moles of phosphoenolpyruvate per each mole of sialylic acid, and catalytic amounts of ATP, myokinase, pyruvate kinase and inorganic pyrophosphatase; and
   (viii) a buffered aqueous reaction medium containing enzymatically sufficient amounts of metal ion cofactors for said enzymes and having a pH value of about 6 to about 8;
   maintaining said reaction mixture at a temperature of about zero degrees C. to about 45° C. for a time period sufficient for said acceptor (vi) to be sialylated and form said sialylα2→3βgalactoside.

9. The process according to claim 8 including the further step of recovering said formed sialylα2→3β-galactoside.

* * * * *